(12) United States Patent
Shivkumar

(10) Patent No.: US 9,603,674 B2
(45) Date of Patent: Mar. 28, 2017

(54) METHOD TO PROTECT THE ESOPHAGUS AND OTHER MEDIASTINAL STRUCTURES DURING CARDIAC AND THORACIC INTERVENTIONS

(75) Inventor: Kalyanam Shivkumar, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 822 days.

(21) Appl. No.: 12/474,151

(22) Filed: May 28, 2009

(65) Prior Publication Data

US 2009/0326511 A1 Dec. 31, 2009

Related U.S. Application Data

(60) Provisional application No. 61/057,732, filed on May 30, 2008.

(51) Int. Cl.
| | | |
|---|---|---|
| A61B 90/00 | (2016.01) | |
| A61B 18/16 | (2006.01) | |
| A61B 18/00 | (2006.01) | |

(52) U.S. Cl.
CPC .............. *A61B 90/04* (2016.02); *A61B 18/16* (2013.01); *A61B 2018/00023* (2013.01); *A61B 2090/0418* (2016.02); *A61B 2090/0481* (2016.02)

(58) Field of Classification Search
CPC ............. A61B 18/16; A61B 19/40; A61B 2018/00023; A61B 2019/4018; A61B 2019/4081; A61B 90/04; A61B 2090/049; A61B 2090/0418; A61B 2090/0427; A61B 2090/0426; A61B 2090/0472; A61B 2090/0481; A61B 2090/049; A61B 2018/00005–2018/00047; A61M 2025/105

USPC .................. 604/506, 103.01, 104; 606/41
See application file for complete search history.

(56) References Cited

U.S. PATENT DOCUMENTS

| | | | | |
|---|---|---|---|---|
| 5,634,895 | A * | 6/1997 | Igo et al. | 604/21 |
| 5,797,960 | A * | 8/1998 | Stevens et al. | 606/213 |
| 5,807,395 | A * | 9/1998 | Mulier et al. | 606/41 |
| 6,231,518 | B1 * | 5/2001 | Grabek et al. | 600/508 |
| 6,802,319 | B2 * | 10/2004 | Stevens et al. | 128/898 |
| 9,055,959 | B2 * | 6/2015 | Vaska et al. | |
| 2003/0125721 | A1* | 7/2003 | Yon et al. | 606/21 |
| 2004/0102771 | A1* | 5/2004 | Bertolero et al. | 606/41 |
| 2004/0102804 | A1* | 5/2004 | Chin | 606/190 |
| 2004/0127895 | A1* | 7/2004 | Flock et al. | 606/41 |
| 2005/0034735 | A1* | 2/2005 | Deem et al. | 128/898 |
| 2005/0149152 | A1* | 7/2005 | Bertolero et al. | 607/96 |
| 2006/0089637 | A1* | 4/2006 | Werneth et al. | 606/41 |

(Continued)

FOREIGN PATENT DOCUMENTS

WO WO 96/32882 A1 10/1996

OTHER PUBLICATIONS

Buch, Eric et al., "A Novel Method for Preventing Phrenic Nerve Injury During Catheter Ablation", *Heart Rhythm*, vol. 4, No. 1, Jan. 2007, pp. 95-98.

*Primary Examiner* — Kami A Bosworth
(74) *Attorney, Agent, or Firm* — Riverside Law LLP

(57) ABSTRACT

Devices and methods are disclosed for preventing injury to a target tissue in proximity to the heart. The methods may include the use a device to externally manipulate the heart to move a portion of the heart away from the target tissue. The methods may also include applying therapy to the heart with the device.

14 Claims, 12 Drawing Sheets

(56) References Cited

U.S. PATENT DOCUMENTS

| | | |
|---|---|---|
| 2007/0055328 A1* | 3/2007 | Mayse et al. .................. 607/105 |
| 2007/0083082 A1* | 4/2007 | Kiser et al. ................... 600/115 |
| 2007/0083225 A1* | 4/2007 | Kiser et al. ................... 606/192 |
| 2008/0033415 A1 | 2/2008 | Rieker et al. |
| 2008/0125708 A1 | 5/2008 | Feng |
| 2008/0161890 A1* | 7/2008 | Lafontaine .................... 607/105 |
| 2008/0243112 A1* | 10/2008 | De Neve ......................... 606/28 |
| 2011/0034936 A1* | 2/2011 | Maloney ....................... 606/108 |

\* cited by examiner

METHOD TO PROTECT THE ESOPHAGUS AND OTHER MEDIASTINAL STRUCTURES DURING CARDIAC AND THORACIC INTERVENTIONS

CROSS-REFERENCES TO RELATED APPLICATIONS

This application claims the benefit under 35 U.S.C. 119 of U.S. Provisional Patent Application No. 61/057,732, filed May 30, 2008, titled "A METHOD TO PROTECT THE ESOPHAGUS AND OTHER MEDIASTINAL STRUCTURES DURING CARDIAC AND THORACIC INTERVENTIONS," which is herein incorporated by reference in its entirety.

STATEMENT AS TO RIGHTS TO INVENTIONS MADE UNDER FEDERALLY SPONSORED RESEARCH OR DEVELOPMENT

A portion of this invention was made with government support under Grant No. R01HL084261 awarded by the National Institutes of Health. The Government has certain rights in the invention.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The invention is related to methods and devices to prevent injury to mediastinal structures such as the esophagus, phrenic nerve, and lung.

BACKGROUND OF THE INVENTION

Catheter ablation for atrial fibrillation (AF) is a procedure that is an effective treatment for common arrhythmia. Arrhythmia, also called dysrhythmia, is an irregular or abnormal heart rhythm. The procedure uses a catheter which gathers data to pinpoint the location of faulty tissue in the heart (e.g. electrical mapping). The catheter is then used to ablate and destroy the faulty tissue. A variety of serious complications have been reported with catheter ablation for AF, including pulmonary vein stenosis, cardiac perforation, thromboembolism, vascular complications, and phrenic nerve injury. Atrioesophageal fistula, thought to result from thermal injury of the esophagus due to its close position to the posterior left atrial (LA) wall, is a rare but often fatal complication of catheter ablation for AF.

Prior methods for detecting and avoiding esophageal injury during left atrial catheter ablation include fluoroscopic contrast visualization to monitor placement of the ablation catheter. Temperature monitoring of the esophagus has also been used. These methods are combined with limiting the amount of energy applied to areas of the heart where collateral damage is likely (e.g. near the esophagus). However, limiting energy delivery near the esophagus may not provide proper therapy, and thus the arrhythmia may not be successfully treated.

BRIEF SUMMARY OF THE INVENTION

One aspect of the invention provides a method for protecting a patient's mediastinal structure while ablating tissue of the patient's heart, comprising, placing a protection member between the mediastinal structure and the heart, expanding the protection member, ablating cardiac tissue, and applying therapy to the heart or the mediastinal structure with the protection member. In some embodiments, the mediastinal structure is an esophagus.

In some embodiments, the protection member comprises a balloon. The protection member can comprise a plurality of openings communicating with a reservoir containing the therapeutic substance. The balloon can be a weeping balloon, for example. In another embodiment, the protection member can comprise an expandable basket.

In some embodiments, the applying therapy step comprises delivering a therapeutic substance from the protection member to the heart. The therapeutic substance can be a drug, a coagulant, or a sealant.

In other embodiments, the applying therapy step comprises chilling the heart with the protection member. The protection member can comprise a balloon containing chilled fluid.

In yet another embodiment, the applying therapy step comprises providing electrical ground on the protection member for use in ablating the heart.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

Figure 1:
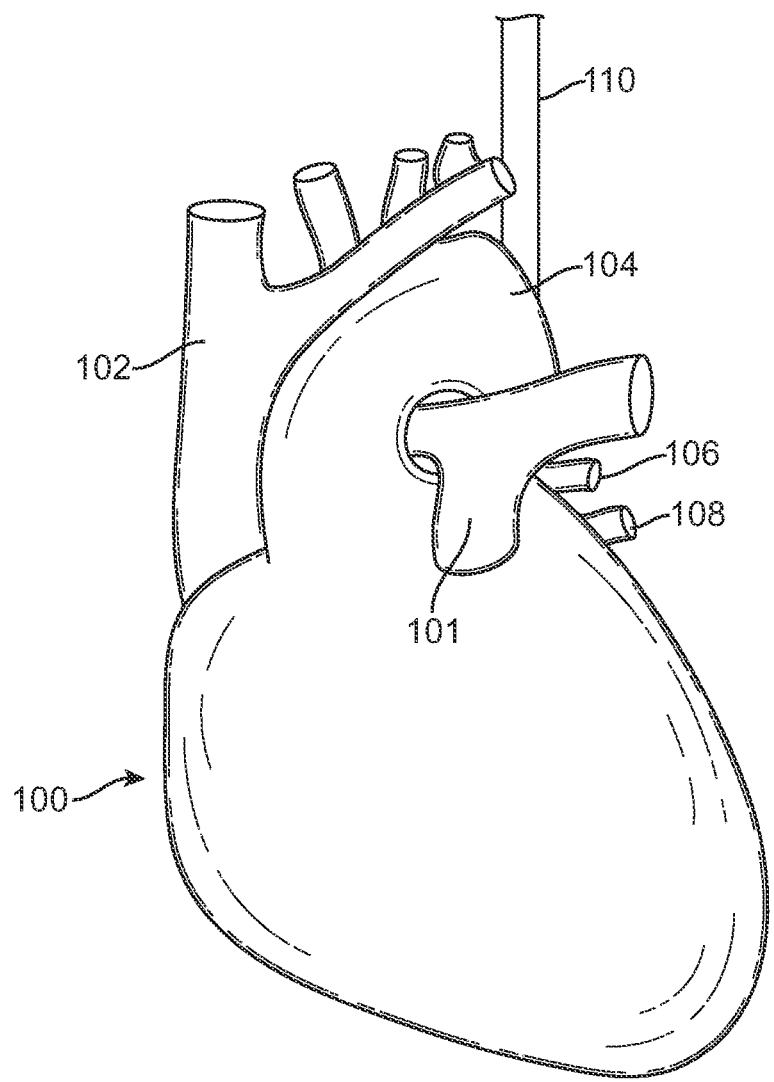
FIG. 1 is an anterior view of the heart.
Figure 2:
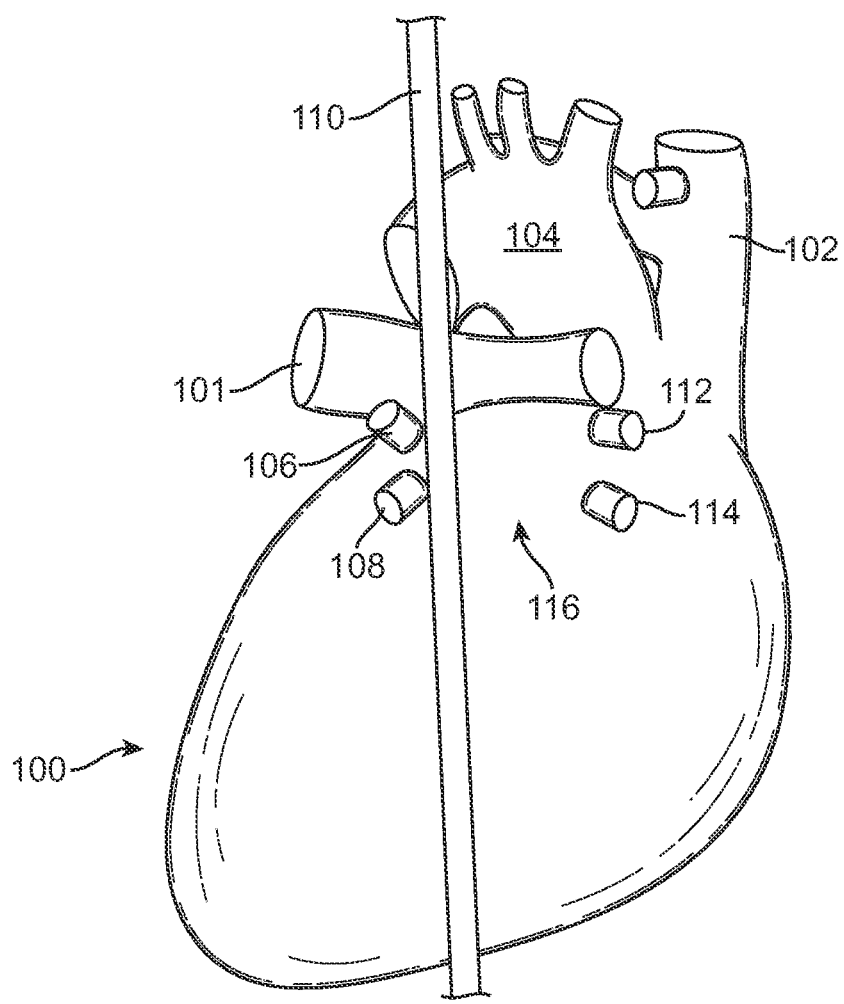
FIG. 2 is a posterior view of the heart showing the esophagus.
Figure 3:
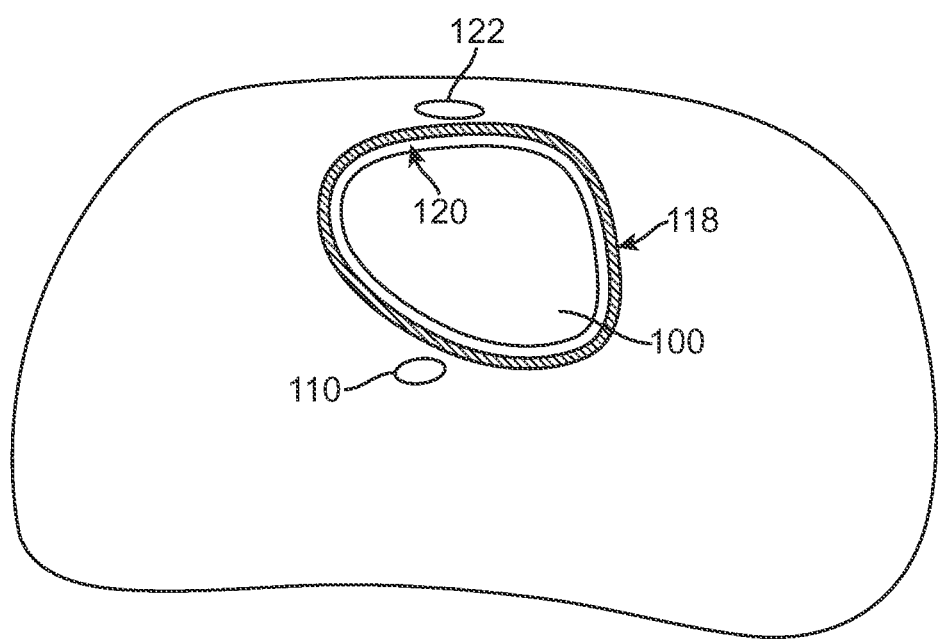
FIG. 3 is a transverse sectional view of the heart and the esophagus.

FIGS. 1-3 show various views of the human heart and surrounding anatomy. FIG. 1 is an anterior view of the heart 100, including the pulmonary artery (PA) 101, superior vena cava (SVC) 102, aorta (AO) 104, left superior pulmonary vein (LSPV) 106 and left inferior pulmonary vein (LIPV) 108. Esophagus 110 can also be seen in FIG. 1. FIG. 2 is a posterior view of the heart, further showing the right superior pulmonary vein (RSPV) 112, right inferior pulmonary vein (RIPV) 114, and left atrium 116. FIG. 3 is a transverse sectional view of the heart 100 and esophagus 110, further showing the pericardium 118, pericardial space 120, and sternum 122. As shown in FIGS. 1-3, the esophagus 110 is in close proximity to the left atrium 116 and the left pulmonary veins 106 and 108.

Figure 4:
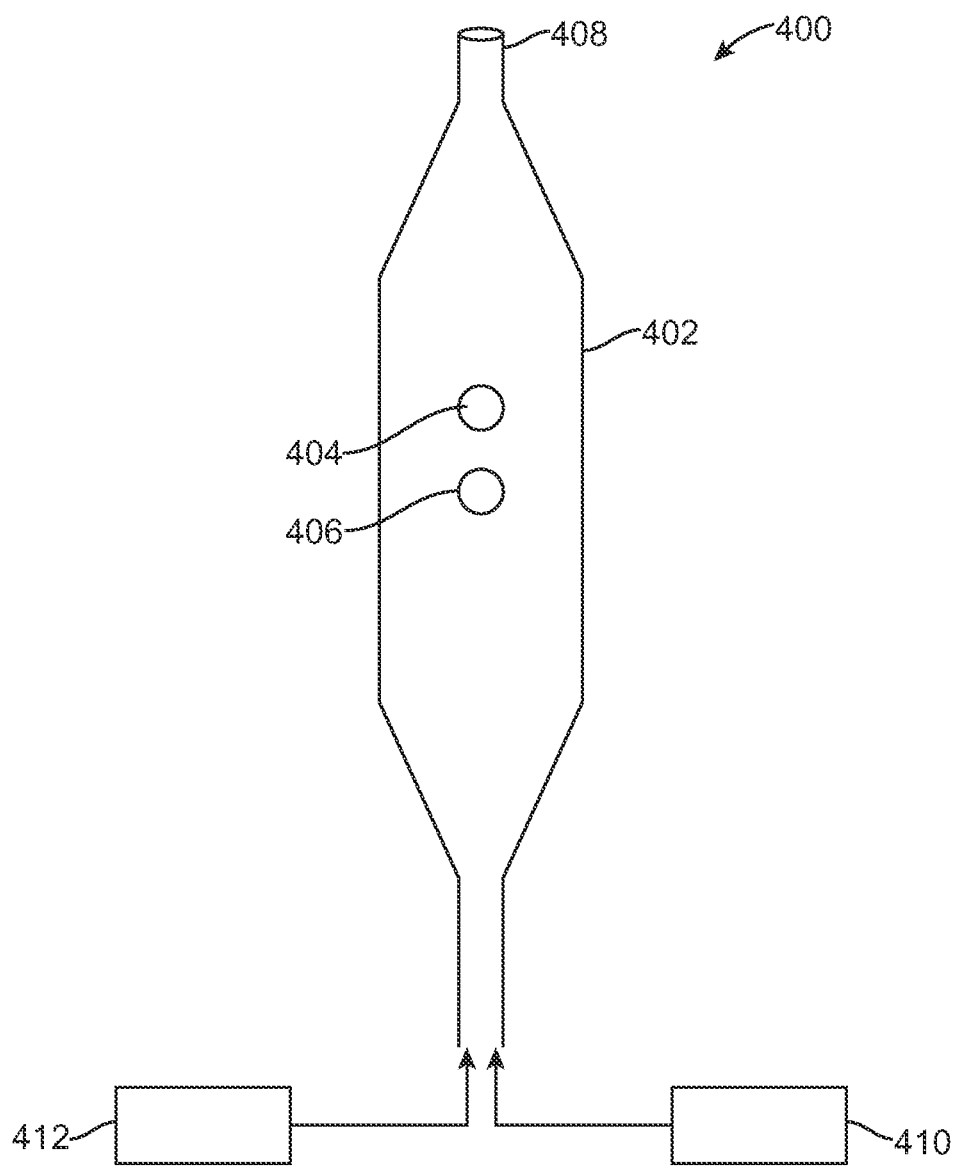
FIG. 4 is a protection member comprising an expandable balloon according to one embodiment of the invention.

FIG. 4 shows one embodiment of a protection member 400 adapted to protect a patient's mediastinal structure during ablation of cardiac tissue and to provide therapy to the heart. A distal portion of the protection member may include a conformable and expandable body 402. In one embodiment, as shown in FIG. 4, the body may be an inflatable balloon catheter. In one specific embodiment, the balloon catheter has a balloon 18-mm×4-cm in size. In FIG. 4, the body is shown in an expanded configuration. However, the body can also be configured to achieve a compact or delivery configuration during navigation to the desired location in the patient. The balloon catheter may include an inflation line for expansion control. The body may be elastic, non-elastic or semi-elastic. The body may also be shaped to prevent injury to mediastinal structures or to cup the heart or move the heart in a preferential direction. In some embodiments, the body can be expanded with chilled liquid to further prevent collateral damage to surrounding tissue. In another embodiment, the body can be expanded with a near body temperature fluid, such as a fluid between approximately 38 degrees C. to 50 degrees C.

Figure 5:
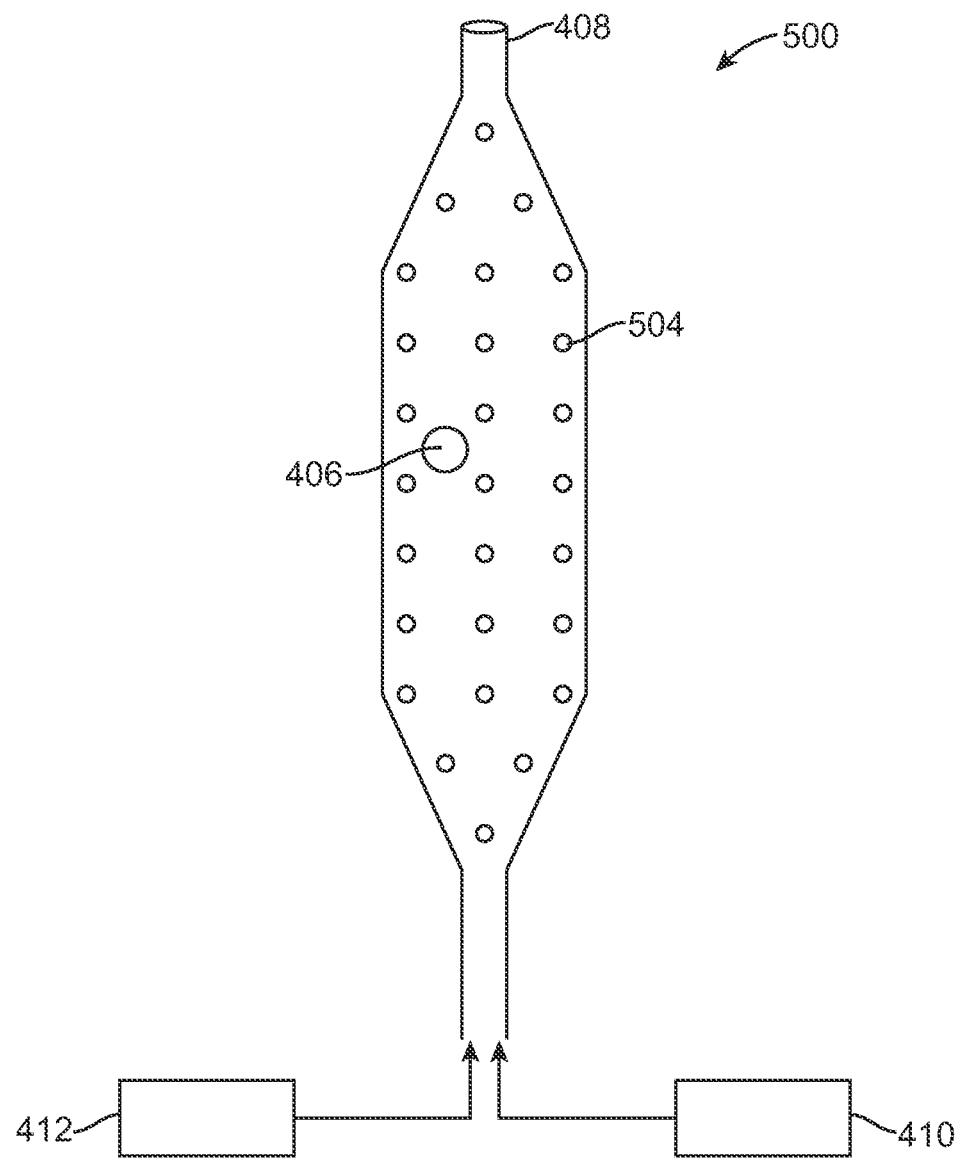
FIG. 5 is a protection member comprising an expandable balloon according to another embodiment of the invention.

As shown in FIG. 4, the protection member can include a therapeutic port or opening 404 on the balloon catheter. The balloon can include any number of therapeutic ports. For example, the protection member 500 of FIG. 5 includes a plurality of therapeutic ports or openings 504. The therapeutic ports can be in fluid communication with a reservoir 410, which may be located within the protection member or, alternatively, external to the device. In some embodiments, the protection member having a plurality of openings can comprise a weeping balloon, for example. In another embodiment, the protection member can be porous. The reservoir may be filled with a therapeutic substance which can be delivered through the ports on the surface of the body to tissue of the heart. In some embodiments, the therapeutic substance is a drug, such as pharmaceutical or biological therapeutic agents known to the medical and surgical professions. The reservoir may also be filled with a coagulant or sealant to help prevent excessive bleeding. In another embodiment, the protection member can include a plurality of reservoirs for delivery of more than one therapeutic substance to the heart tissue.

The protection member can also include diagnostic ports or openings 406. The diagnostic ports 406 may be connected to separate diagnostic and therapeutic devices 412, such as robotic controls to provide improved visualization or delivery of therapeutic agents, air and water channels, vacuum channels, or imaging devices such as a miniature camera or fiber optic imaging bundle, for example.

Figure 6:
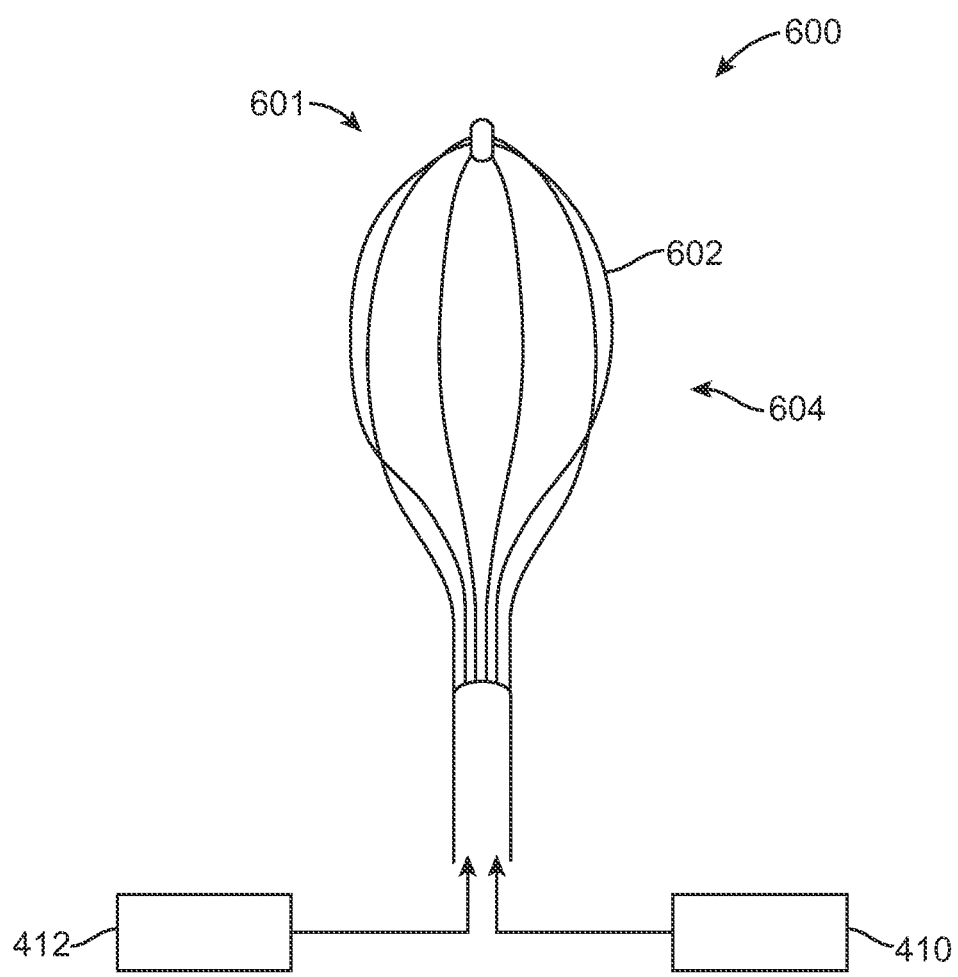
FIG. 6 is a protection member comprising an expandable basket according to one embodiment of the invention.

The protection member may comprise other mechanical devices, such as expandable baskets. FIG. 6 illustrates a protection member 600 comprising an expandable basket 601 made up of splines 602. In FIG. 6, the body is shown in an expanded configuration. However, the body can also be configured to achieve a compact or delivery configuration during navigation to the desired location in the patient. The expandable basket may include therapeutic ports 604 integral to the splines for delivering a therapeutic substance to tissue. Alternatively, the basket may include spray nozzles or therapeutic delivery tubes within the basket for delivering a therapeutic substance to tissue.

The protection members described herein can include a steering mechanism for selectively steering or bending the device in the desired direction within a patient, and can also include a guide wire lumen 408 for advancing the device over a guide wire.

Figure 7:
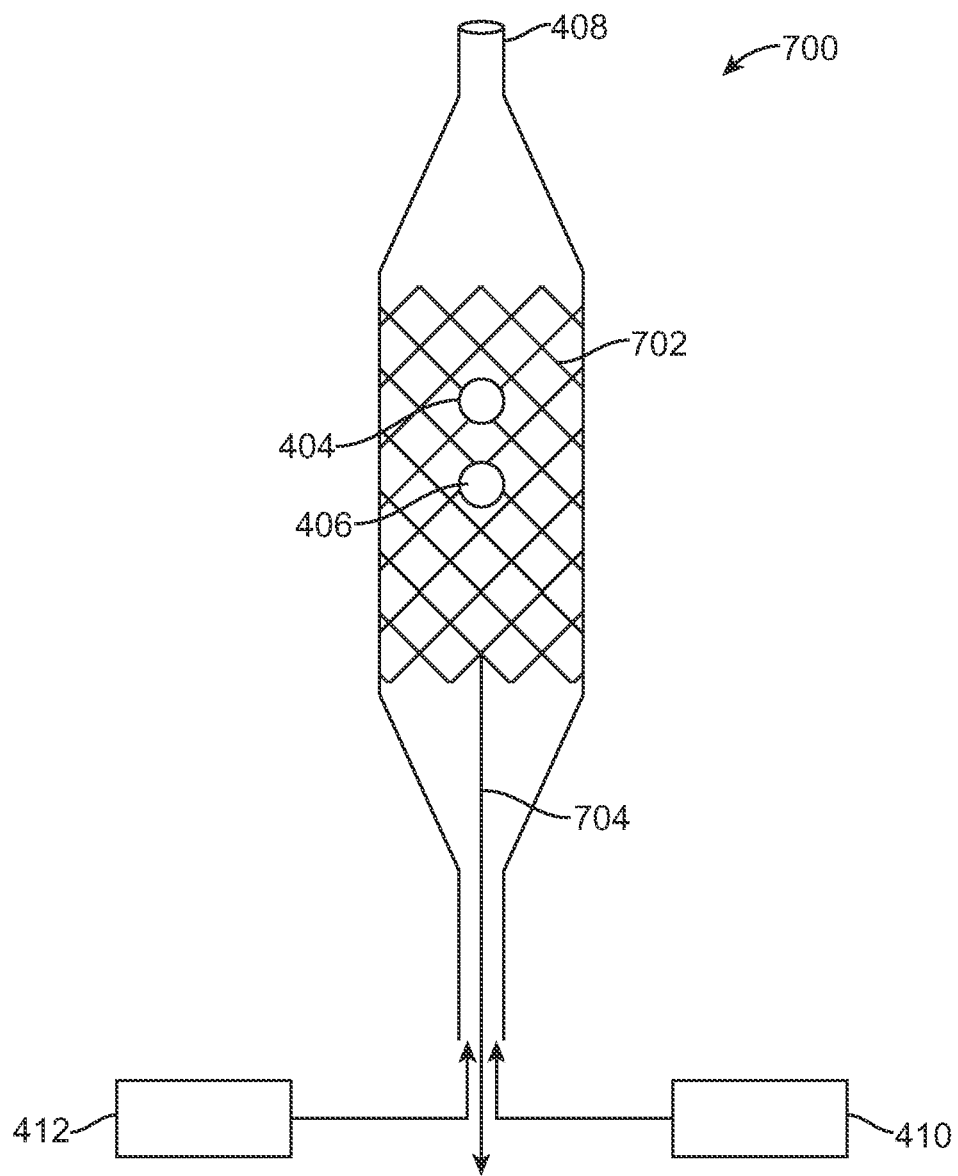
FIG. 7 is a protection member comprising an expandable balloon and a mesh surface according to one embodiment of the invention.

The body may help monitor portions of the heart during surgery and also provide additional therapies, such as ECG monitoring for mapping or other purposes. The protection member may include grounded elements which would immediately ground an electrical ablation device which punctures the pericardium to prevent further ablation and collateral damage. For example, as shown in FIG. 7, the protection member may include an expandable mesh surface 702 coupled to a ground lead 704. In another embodiment, the protection member may include a metal plate coupled to a ground lead.

Figure 8:
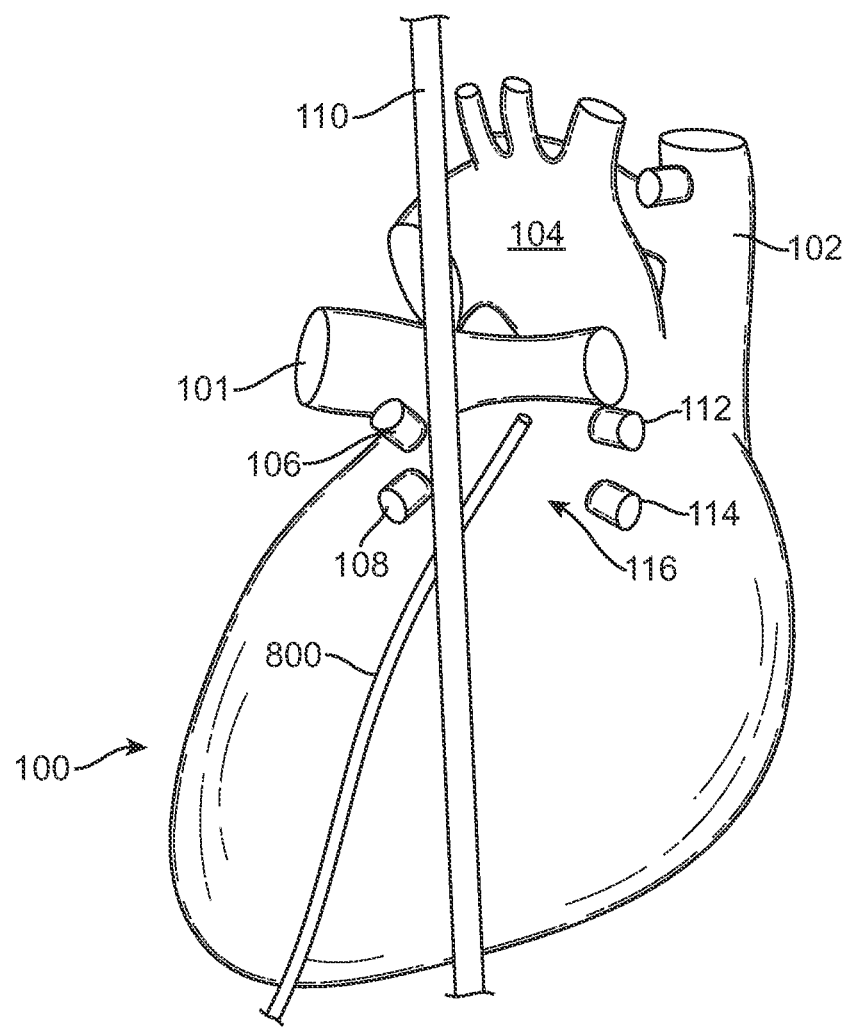
FIGS. 8-9 illustrate a protection member in a delivery configuration placed between the heart and the esophagus.
Figure 9:
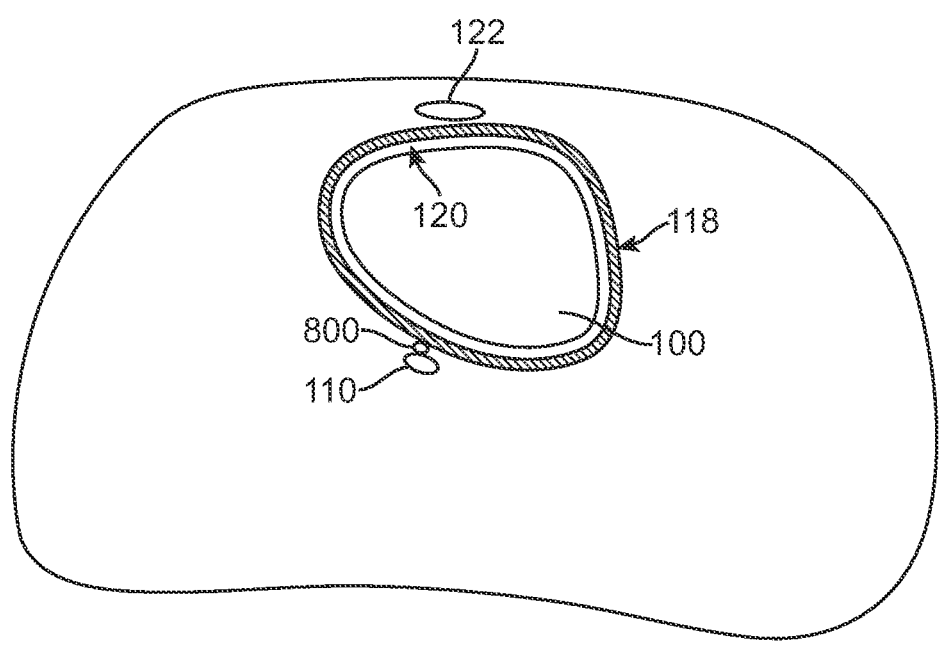
Figure 10:
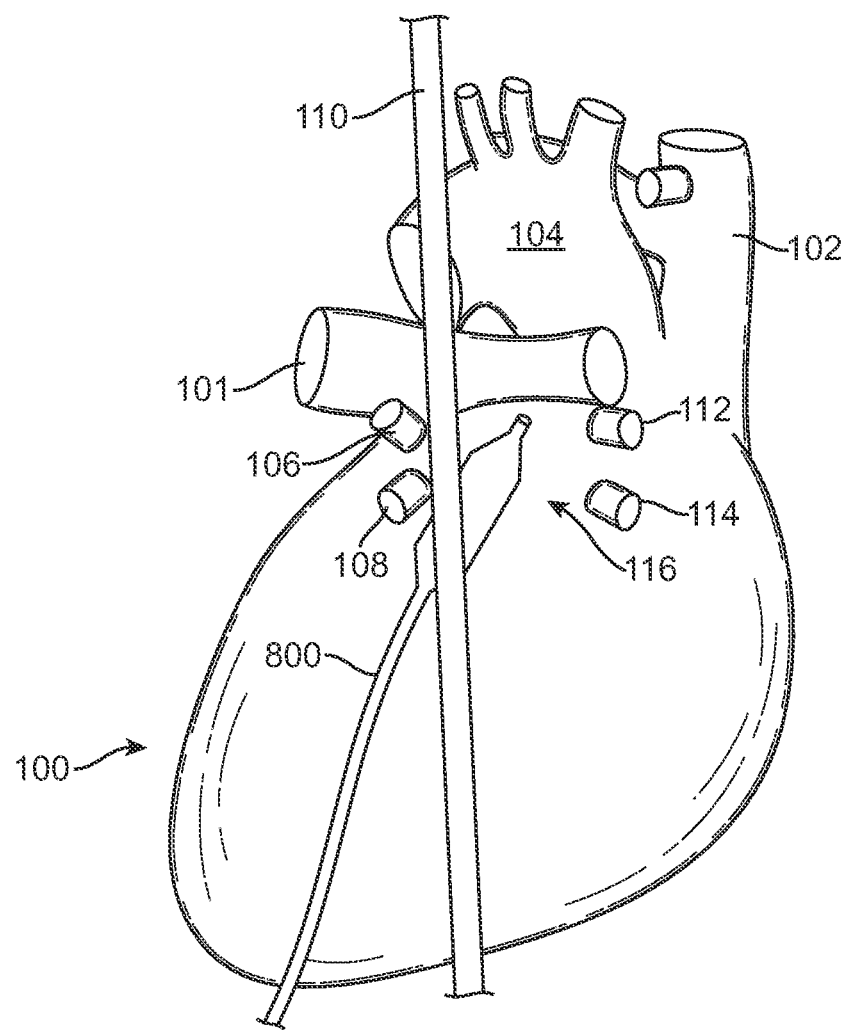
FIGS. 10-11 illustrate a protection member in an expanded configuration placed between the heart and the esophagus.
Figure 11:
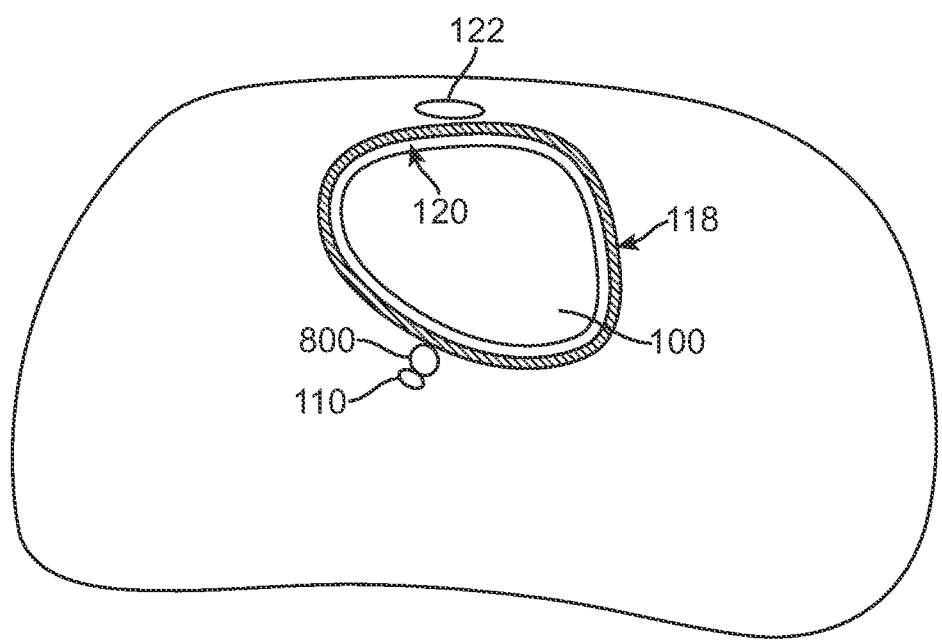

Methods of using the protection member to manipulate the heart to protect a target tissue and apply therapy to the tissue, such as a mediastinal structure, will now be discussed. As shown in FIGS. 8-9, a protection member 800 in its compact or delivery configuration can be placed between a portion of the heart and a target tissue. The protection member can be any of the protection members described herein. For example, the protection member can comprise an expandable balloon or an expandable basket. The target tissue can be any mediastinal tissue in close proximity to the heart, such as the esophagus, phrenic nerve, or lung. For purposes of description, however, FIGS. 8-12 show the protection member being used to protect the esophagus.

The protection member can be delivered to its position between the target tissue and the heart by any method known in the art. For example, to place the protection member between the heart and the esophagus, the subxiphoid approach can be used to gain access to the pericardial space, and the protection member can be advanced through the pericardial space over a guide wire to the oblique sinus immediately adjacent to the posterior left atrium, between the left atrium and the esophagus.

When the protection member is positioned between the target tissue and the heart, the protection member can be expanded. When the protection member is placed between the esophagus and the heart, for example, expanding the device can cause deflecting of the left atrium to a suitable distance from the target tissue. For example, during a cardiac ablation procedure, it may be necessary to separate the left atrium at least a distance of 10-30 mm from the esophagus to safely ablate the cardiac tissue.

A separate ablation device may then be activated within the heart to perform catheter ablation in the cardiac tissue, such as the left atrium or in or proximate to the pulmonary veins, without concern for collateral damage to the target tissue, such as the esophagus. The protection member enables full energy catheter ablation for atrial fibrillation to be applied to all regions of the heart while minimizing the risk of collateral damage to surrounding tissue. Thus a patient may fully recover from arrhythmia and not require retreating, open-heart surgery, or life-long drug therapy. In one embodiment, the protection member includes an electrical ground to immediately ground the separate ablation device should it puncture the pericardium.

Figure 12:
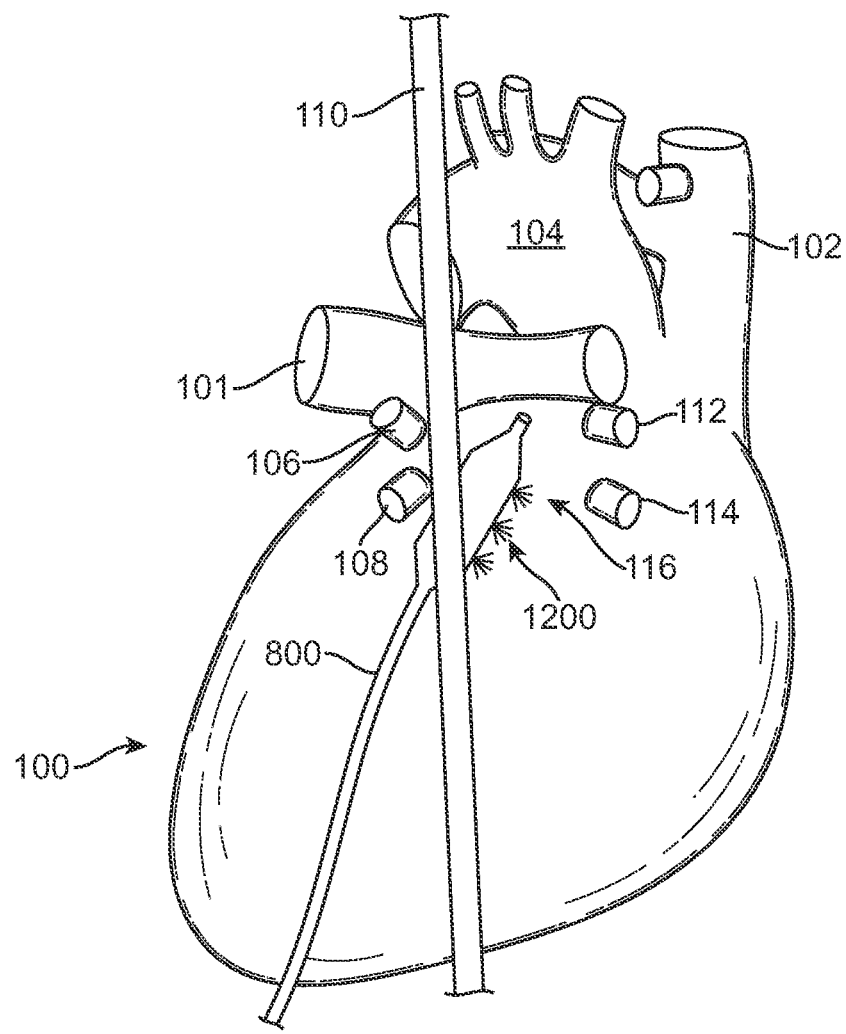
FIG. 12 illustrates a protection member applying therapy to the heart.

Prior to, during, or after ablation of cardiac tissue, the protection member may apply therapy to the heart or mediastinal structure. In one embodiment, the protection member can be filled with a chilled fluid or medium to chill the heart or mediastinal structure. In another embodiment, as shown in FIG. 12, the protection member can apply therapy to the heart or mediastinal structure by delivering a therapeutic substance 1200 to the heart or mediastinal structure. The therapeutic substance can be any substance described herein, such as a drug, a coagulant, or a sealant. In some embodiments, the therapeutic substance is delivered through a plurality of openings communicating with a fluid reservoir containing the therapeutic substance.

The use of the protection member is not limited to catheter ablation for atrial fibrillation. Any therapy within the heart may be aided by external manipulation of the heart.

Case Report:

A 57-year-old male with history of highly symptomatic paroxysmal AF, refractory to amiodarone and propafenone therapy, was referred for consideration of catheter ablation. The patient had a structurally normal heart, with past medical history significant only for Graves Disease, controlled with propylthiouracil. The patient had undergone circumferential pulmonary vein (PV) ablation 18 months earlier, but complete PV isolation could not be achieved due to the position of the esophagus, which was directly adjacent to the left-sided pulmonary veins as seen by esophageal contrast imaging. During the first procedure, care was taken to avoid radiofrequency application near the esophagus, and there were no complications. The patient had some improvement in symptoms following this procedure, but 12 months later had recurrence of palpitations and fatigue. The patient was found to have frequent episodes of atrial fibrillation despite a trial of antiarrhythmic medication. A MRI showed normal left ventricular function and mild left atrial enlargement. The esophagus was seen to lie directly adjacent to the ostium of the left inferior PV. The patient was referred for a second radiofrequency catheter ablation procedure, this time with epicardial access to attempt more complete PV isolation and protect the esophagus if necessary.

After induction of general anesthesia, standard multipolar electrophysiology catheters were advanced through the femoral veins to the right atrium, right ventricular septum, and the bundle. A coronary sinus catheter was placed using the internal jugular vein. Epicardial access was obtained via subxiphoid puncture and an SL 0 (zero) sheath (St. Jude Medical) was advanced into the pericardial space. A double transseptal puncture was performed to pass two SL0 sheaths into the left atrium. Intravenous heparin was given to maintain activated clotting time over 300 seconds. Liquid barium suspension was delivered by orogastric tube to allow fluoroscopic visualization of the esophagus, and a probe was advanced into the esophagus for continuous temperature monitoring during the ablation procedure. A Lasso circular multipolar catheter (Biosense Webster, Diamond Bar, Calif.) was used for mapping the pulmonary veins, and a Celsius Thermocool 3.5-mm irrigated tip catheter (Biosense Webster, Diamond Bar, Calif.) was used for circumferential pulmonary vein ablation. No difficulty was encountered in mapping and isolating the left superior, right superior, and right inferior pulmonary veins. However, the medial antral region of the LIPV was immediately adjacent to the esophagus on multiple fluoroscopic views. This vein could not be isolated due to concern about thermal esophageal injury.

In order to safely ablate near the LIPV, a Meditech 18-mm×4-cm balloon catheter (Meditech, Boston Scientific) was advanced through the pericardial space over a guide wire, to the oblique sinus immediately adjacent to the posterior left atrium. When it was positioned between the left atrium and the esophagus, the balloon was inflated, deflecting the LIPV and its antrum laterally and away from the esophagus. Electroanatomical mapping (EnSite system, St. Jude Medical, St. Paul, Minn.) was used to show the proximity of the LIPV to a quadripolar electrophysiology catheter in the esophagus before and after balloon inflation. With the increased separation and intervening balloon catheter, endocardial antral isolation could be completed safely.

No heating of the esophagus was observed, and electrical isolation of the vein was successful. At the conclusion of the procedure, a pericardial drain was left in place due to moderate bleeding in the pericardial space. There was no evidence of tamponade, the bleeding stopped without intervention, and the drain was removed the following day. The patient was discharged home on the second post-procedure day.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method for protecting a patient's mediastinal structure while ablating tissue of the patient's heart, the method comprising:
    placing a protection member between the mediastinal structure and the posterior heart by a subxiphoid approach;
    expanding the protection member, thereby separating the mediastinal structure from the heart;
    ablating cardiac tissue from within the heart; and
    applying simultaneous therapy to the heart and the mediastinal structure with the protection member.

2. The method of claim 1 wherein the protection member comprises a balloon.

3. The method of claim 1 wherein the applying step comprises chilling the heart with the protection member.

4. The method of claim 3 wherein the protection member comprises a balloon containing chilled fluid.

5. The method of claim 1 wherein the applying step comprises delivering a therapeutic substance from the protection member to the heart.

6. The method of claim 5 wherein the therapeutic substance comprises a drug.

7. The method of claim 5 wherein the protection member comprises a plurality of openings communicating with a reservoir containing the therapeutic substance.

8. The method of claim 7 wherein the protection member comprises a weeping balloon.

9. The method of claim 1 wherein the applying step comprises providing electrical ground on the protection member for use in ablating the heart.

10. The method of claim 1 wherein the protection member comprises an expandable basket.

11. The method of claim 1 wherein the mediastinal structure is an esophagus.

12. The method of claim 1, wherein the therapy comprises chilling the mediastinal structure with the protection member.

13. The method of claim 1, wherein the therapy comprises delivering a therapeutic substance from the protection member to the mediastinal structure.

14. The method of claim 1, further comprising introducing the protection member to the patient transthoracically.

* * * * *

UNITED STATES PATENT AND TRADEMARK OFFICE
CERTIFICATE OF CORRECTION

PATENT NO. : 9,603,674 B2
APPLICATION NO. : 12/474151
DATED : March 28, 2017
INVENTOR(S) : Kalyanam Shivkumar Page 1 of 1

It is certified that error appears in the above-identified patent and that said Letters Patent is hereby corrected as shown below:

In the Specification

On Column 1, please delete the paragraph from Line 20 to Line 23, and replace it with the following paragraph:

-- This invention was made with Government support under Grant Number HL084261, awarded by the National Institutes of Health. The Government has certain rights in the invention. --

Signed and Sealed this
Second Day of May, 2017

Michelle K. Lee
*Director of the United States Patent and Trademark Office*